Figure 1:
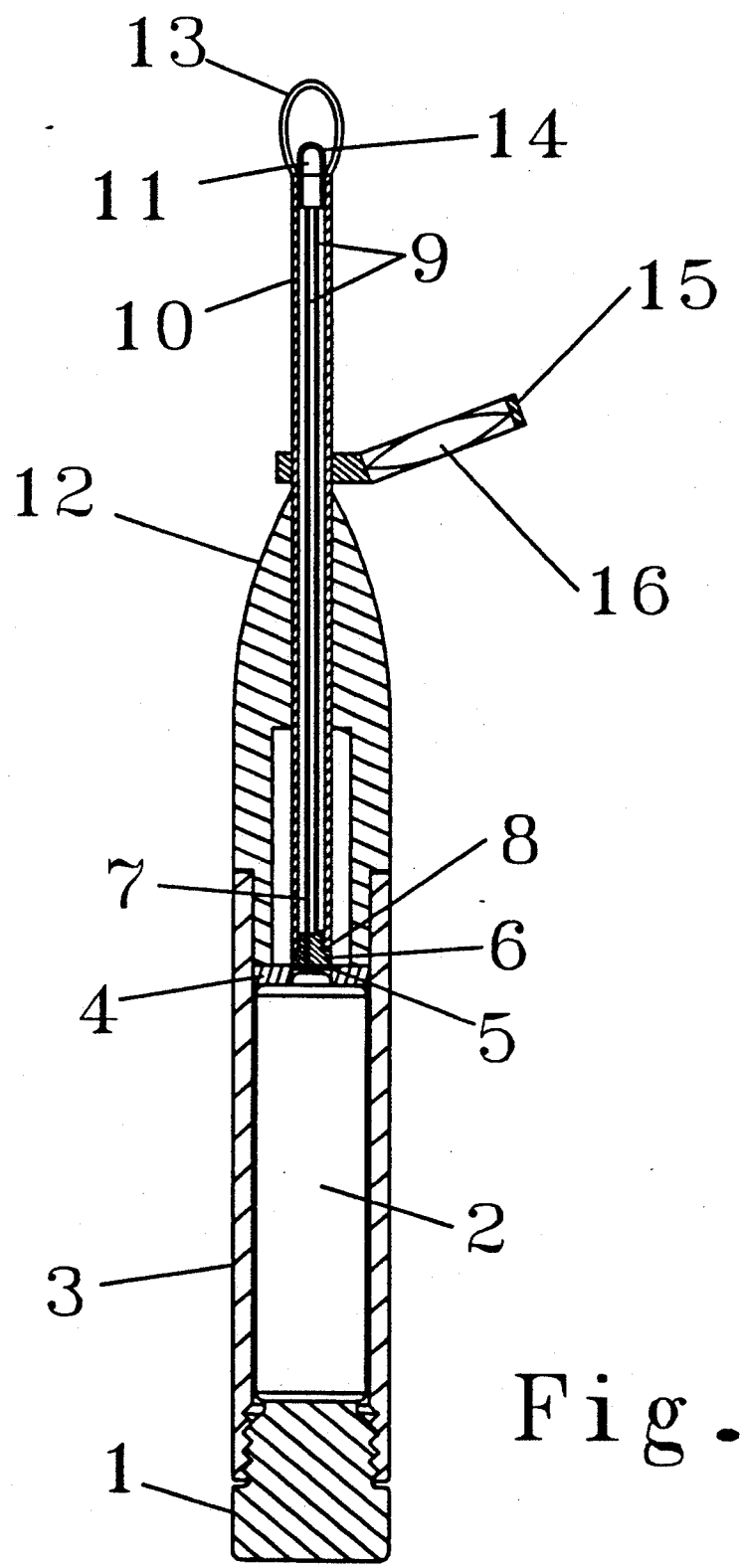

United States Patent [19]
Krug et al.

[11] Patent Number: 5,209,757
[45] Date of Patent: May 11, 1993

[54] ILLUMINATED EAR CLEANING DEVICE

[76] Inventors: John A. Krug, 2689 N. Galley St., Orange, Calif. 92665; Romeo S. Ortiz; Marylin R. Ortiz, both of 1004 Vine St., Paso Robles, Calif. 93446

[21] Appl. No.: 730,281

[22] Filed: Jul. 15, 1991

[51] Int. Cl.⁵ .............................................. A61F 11/00
[52] U.S. Cl. .................................................. 606/162
[58] Field of Search .................. 606/161, 162; 433/29; 128/759

[56]         References Cited
U.S. PATENT DOCUMENTS 4,572,180  2/1986  Deenadayal ..................... 606/161
4,785,796  11/1988  Mattson ........................... 606/161
4,800,896  1/1989  Jalowayski ....................... 606/161

Primary Examiner—C. Fred Rosenbaum
Assistant Examiner—William W. Lewis

[57]            ABSTRACT

An illuminated ear cleaning device with the illuminating means in close proximity to an ear cleaning means. The illuminating means and or the ear cleaning means may be replaceable or sterilizable and reusable. The illuminated ear cleaning device includes a handle means containing an energy means which may be permanent, rechargeable or throw-a-way and a switch means to turn the illuminating means on and off. A magnifying means is also included to provide magnification at the point of use.

1 Claim, 2 Drawing Sheets

ILLUMINATED EAR CLEANING DEVICE

FIELD OF THE INVENTION

The present invention relates to an improved ear cleaning device. More specifically, it concerns an illuminated ear cleaning device with the illuminating means in close proximity to or part of an ear cleaning means which provides illumination at the point of use and incorporates a magnifying means.

BACKGROUND OF THE INVENTION

In the cleaning of ears by physicians the normal practice is to look into the ear and locate the wax or other obstruction to be removed and then use an unlighted cleaning device to remove the obstruction. Often the physician will use a flash light or other illumination device in conjunction with the unlighted cleaning device. When the physician uses both the unlighted ear cleaning tool and a flash ight another person may be needed to hold the head of the patient. These types of ear cleaning devices are in common use and may be public domain. Our search uncovered primarily two types of ear cleaning devices. One type is made of stainless steel and has a rounded stainless steel wire loop connected to a handle about six inches long. The other type of ear cleaning device was made of molded plastic with a curved thin ribbon loop of plastic at one end of an approximately five inch curved handle. There were no patent numbers on either type of the ear cleaning devices as described above. A patent search was conducted at the Washington D. C. Patent Office which uncovered no patents with the illuminating lamp in close proximity to or part of the ear cleaning or scraping tip. Our invention also uses a cleaning tip similar to those in common use or possibly in public domain but in conjunction with a lamp as part of or in close proximity to the cleaning tip which is the object of our invention. The cleaning tip could also be of a different shape such as a hook rather than a loop. For this reason we do not intend to limit our invention to that which is common even though we show a common cleaning tip in our drawing. This is an improvement over the existing ear cleaning devices in that the physician can see the inside of the ear without the need for a flashlight or other separate illuminating device and the illumination is at the point of use and part of the cleaning tip, both of which are sterilizable and replaceable. In addition, we have incorporated a magnifying means to further enhance and improve the ability of a physician to see a magnified view of the inside of the ear wherein the magnifying means is designed to provide focus in the area of the illuminated cleaning tip.

OBJECTS AND ADVANTAGES

It is accordingly an object of this invention to provide a convenient, compact, lightweight, self contained illuminated ear cleaning device to improve the controllability and quality of ear cleaning so that the illuminating means will provide illumination at the point of use and the magnifying means will further improve ear cleaning controllability and control by magnifying the point of use area.

It is also an object of this invention to provide additional convenience by incorporating permanent, rechargeable or throw-a-way energy means.

Another object of the invention is to provide a handle designed for convenience and comfort during use by a physician.

Figure 2:
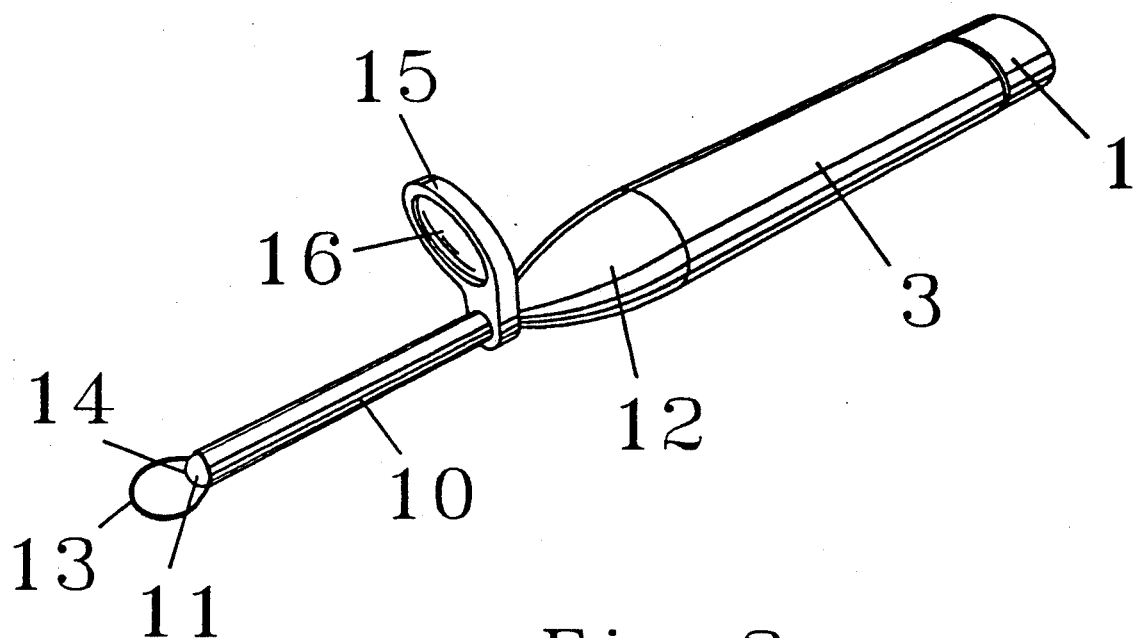
Figure 3:
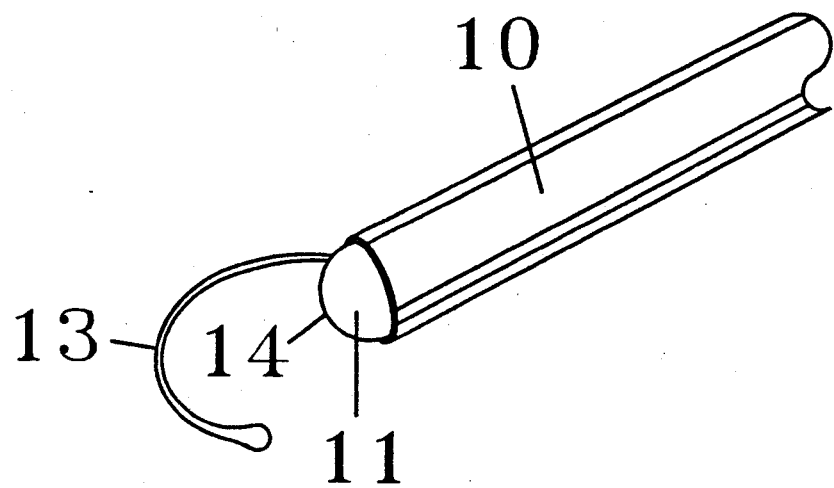

These and other objects will be in part pointed out in and in part apparent from but not limited in form by the following description of an embodiment of the invention, considered in conjunction with the accompanying drawings in which:

FIG. 1 is a section view of the entire device.
FIG. 2 is a perspective view of the entire device.
FIG. 3 is a detail showing a hook type ear cleaning or scraping tip.

DESCRIPTION

To turn on the illuminated ear cleaning device the physician would hold the device in one hand and turn the threaded switch actuator 1 clockwise with his other hand which will move the battery(s) 2 through the main housing tube 3 thereby collapsing the insulating spring 4 and making contact with connector plate 5 which is attached to the insulator plug 6 which is also the part used for connection of both the positive 7 and negative 8 lamp wires 9 which travel through a tube 10 to lamp 11 which would be used to illuminate the inside of an ear. The tube 10 which may be removable and or replaceable is fitted into the front housing 12 which is connected to the main housing tube 3. The cleaning tip 13 which is used to clean or scrape the inside of an ear is connected to tube 10 and the lamp 11 is fitted inside and protrudes from tube 10 and lamp 11 is coated with a clear substance 14 which protects the lamp and the patient from possible breakage of or heat from the lamp 11. The frame 15 holds the magnifying lens 16 and frame 15 is also fitted onto or part of tube 10 thereby providing a magnified view at the point of use. The frame 15 and magnifying lens 16 may be removable and may be a part of or removable from the front housing 12.

To turn off the illuminated ear cleaning device the physician would turn the threaded switch actuator 1 counterclockwise relative to the device thereby allowing the battery(s) 2 to be pushed back through the main housing 3 by the insulating spring 4 to the original position.

What is claimed is:

1. A hand held, illuminated ear cleaning device comprising;
   a main housing containing a power source and capable of being utilized as a handle for the device;
   a flexible, enlongated tube having proximal and distal ends, said proximal end connected to the housing and an ear cleaning tip and an illumination means are attached to the distal of the tube;
   an electrical conducting means in a lumen of said tube to connect the illumination means and the power source;
   said illumination means consist of either a light bulb or a light emitting diode;
   said power source comprising a battery.

* * * * *